United States Patent [19]

Kimura et al.

[11] Patent Number: 5,556,848
[45] Date of Patent: Sep. 17, 1996

[54] OPHTHALMIC SUSPENSION CONTAINING DIFLUPREDONATE

[75] Inventors: Motoko Kimura, Hiroshima; Yasushi Morita, Toyonaka; Takahiro Ogawa, Nishinomiya; Tadashi Terai, Kobe, all of Japan

[73] Assignees: Senju Pharmaceutical Co., Ltd., Osaka; Mitsubishi Chemical Corporation, Tokyo, both of Japan

[21] Appl. No.: 359,654

[22] Filed: Dec. 20, 1994

[30] Foreign Application Priority Data

Dec. 27, 1993 [JP] Japan ................... 5-332099

[51] Int. Cl.⁶ ........................... A61K 31/56
[52] U.S. Cl. ............................. 514/179
[58] Field of Search ....................... 514/179

[56] References Cited

U.S. PATENT DOCUMENTS

| | | | |
|---|---|---|---|
| 3,780,177 | 12/1973 | Ercoli et al. | 424/243 |
| 3,784,692 | 1/1974 | Ercoli et al. | 424/243 |
| 4,304,765 | 12/1981 | Shell et al. | 424/14 |
| 4,478,818 | 10/1984 | Shell et al. | 424/14 |
| 5,401,510 | 3/1995 | Robertson et al. | 424/427 |
| 5,407,926 | 4/1995 | Clark | 514/179 |
| 5,446,070 | 8/1995 | Mandelli | 514/772.6 |

OTHER PUBLICATIONS

Mitsubishi Chemical, Chemical Abstracts, vol. 118, No. 24 14 Jun. 1993 Abstract No. 240992 JP-A-05043465.
Mitsubishi Petroch, KK, Database WPI, Week 8636, Derwent Publications Ltd. London GB AN86-236771 (36) JP-A-61 167 614, 1991.

*Primary Examiner*—Marianne M. Cintins
*Assistant Examiner*—Keith MacMillan
*Attorney, Agent, or Firm*—Wenderoth, Lind & Ponack

[57] ABSTRACT

An ophthalmic suspension comprising difluprednate as an active ingredient. The ophthalmic suspension of the present invention shows superior antiinflammatory action and antiallergic action by local administration. Accordingly, the suspension of the present invention is useful for the treatment and prevention of disorders of the eye, such as allergic conjunctivitis, vernal conjunctivitis, blepharitis marginalis, catarrhal conjunctivitis and uveitis.

12 Claims, 2 Drawing Sheets

OPHTHALMIC SUSPENSION CONTAINING DIFLUPREDONATE

FIELD OF THE INVENTION

The present invention relates to an ophthalmic suspension containing difluprednate, which is an antiinflammatory steroid, as an active ingredient.

BACKGROUND OF THE INVENTION

Difluprednate ($6\alpha,9\alpha$-difluoroprednisolone 17-butyrate 21-acetate) is an antiinflammtory steroid developed for local application, and is known to show superior antiinflammatory action by percutaneous administration (U.S. Pat. Nos. 3780177, 3784692). Difluprednate reportedly shows superior anti-inflammatory action and antiallergic action by percutaneous administration and subcutaneous administration [Pharmacometrics, 29 (3), 343–353 (1985), Pharmacometrics, 29 (3), 355–362 (1985)]. In view of such pharmacological actions, difluprednate is currently used mainly as a therapeutic drug for skin disorders such as eczema and dermatitis in the form of an ointment or a cream.

It is also expected that difluprednate will be effective for the treatment of various eye disorders by local administration to the eye, since difluprednate has superior antiinflammatory action and antiallergic action. The aforementioned U.S. Pat. Nos. 3780177, 3784692 detail formulation of difluprednate into an eye ointment for local administration to the eye. However, when a local administration to the eye is desired, an eye ointment is not entirely easy to use. Accordingly, formulation into an eye drop is preferred for the reason of easy administration. However, difluprednate has low solubility in water and preparation of a stable eye drop containing difluprednate at a therapeutically effective concentration is difficult. Thus, a pharmaceutical preparation of difluprednate which can be instilled to the eye has not been provided.

SUMMARY OF THE INVENTION

An object of the present invention is to provide a novel pharmaceutical preparation of difluprednate, which permits instillation to the eye.

Another object of the present invention is to provide an agent containing difluprednate for local administration to the eye, which exhibits superior reparation stability.

It has now been found that a suspension of difluprednate provides a novel pharmaceutical preparation which can be instilled to the eye.

It has been also found that a suspension of difluprednate may, when left standing for a long time, form secondary particles due to partial agglomeration caused by mutual adhesion of suspended particles, or a hard deposit layer (caking) on the bottom surface of a container; or may have a lowered pH. Such formation of secondary particles or caking causes problems in terms of particle size and redispersibility (hereinafter secondary particles and caking are sometimes integrally referred to as agglomerates). The present inventors have investigated the stability of various difluprednate suspensions and found that adding suitable ingredients to the suspension results in the provision of a superior suspension in terms of redispersibility and stability, wherein secondary particles and caking due to agglomeration, as well as decrease in pH are suppressed.

BRIEF DESCRIPTION OF THE DRAWINGS

In FIG. 2, ○ is difluprednate and ● is betamethasone.

DETAILED DESCRIPTION OF THE INVENTION

Figure 1:
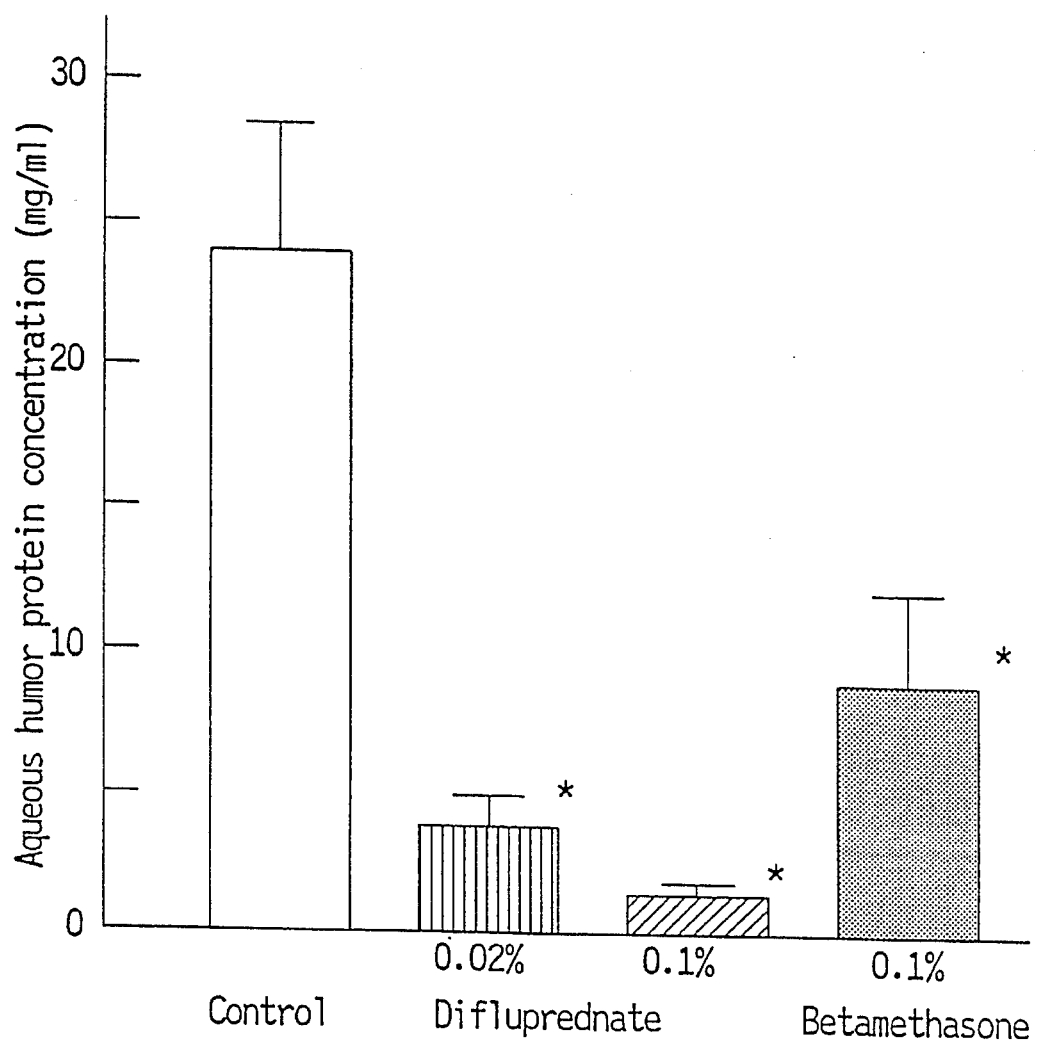
FIG. 1 is a graph showing the results of Experimental Example 2, wherein each value is the mean±standard error (n=6–7) and the mark "*" indicates presence of a significant difference from the control, $p<0.01$.

In the present invention, a suspension means a liquid agent having solid particles homogeneously dispersed in the liquid. The ophthalmic suspension of the present invention comprises a pharmaceutically acceptable solvent and difluprednate, with the difluprednate dispersed in said solvent. The pharmaceutically acceptable solvent may be, for example, an aqueous solvent such as water, physiological saline and buffer. While the difluprednate content may vary depending on diseases to be treated and the like, difluprednate is generally contained in a proportion of 0.005–0.5 w/v %, preferably 0.01–0.2 w/v % relative to the entire suspension.

The suspension of the present invention may comprise a water soluble polymer for enhancing dispersion stability. Examples of the water soluble polymer include hydroxypropyl-methylcellulose, polyvinyl alcohol, hydroxyethylcellulose, hydroxypropylcellulose, polyvinylpyrrolidone, polyethylene glycol, sodium carboxymethylcellulose, methylcellulose, ethylcellulose, sodium arginate, gelatin and carboxyvinyl polymer. Other suspending agents known in the field of pharmaceutical preparation may be also contained.

Of the above-mentioned water soluble polymers, hydroxypropylmethylcellulose and polyvinyl alcohol are preferable, since they suppress formation of agglomerates, prevent lowering of pH, and provide a suspension superior in redispersibility and stability. A methoxy group and a hydroxypropoxy group in the hydroxypropylmethylcellulose are preferably contained in a proportion of 19–30% and 4–12%, more preferably 28–30% and 7–12%, respectively. The average molecular weight of polyvinyl alcohol is preferably about 30,000–150,000, more preferably about 100,000–120,000. The water soluble polymer is generally contained in a suspension in a proportion of 0.01–2.0 w/v %, preferably 0.02–1.0 w/v %, more preferably 0.05–0.2 w/v %.

The suspension of the present invention may comprise a preservative for preventing contamination with microorganisms such as fungi and bacteria. The preservative usable in the present invention has antibacterial action and antifugal action, and should be non-toxic, non-irritant and applicable to the eye. Examples of the preservative include quaternary ammonium salts such as benzalkonium chloride and benzethonium chloride; cationic compounds such as chlorhexidine gluconate; p-hydroxybenzoates such as methyl p-hydroxybenzoate, ethyl p-hydroxybenzoate, propyl p-hydroxybenzoate and butyl p-hydroxybenzoate; alcohol compounds such as chlorobutanol and benzyl alcohol; sodium dehydroacetate; and thimerosal. Of the recited preservatives, quaternary ammonium salts and cationic compounds are preferable as they suppress formation of agglomerates, prevent lowering of pH, and provide a suspension superior in redispersibility and stability. Of the quaternary ammonium salts, benzalkonium chloride and benzethonium chloride are particularly preferable, and chlorhexidine gluconate is particularly preferable as the cationic compound. The preservative is generally contained in a proportion of 0.001–0.3 w/v %, preferably 0.002–0.05 w/v % and more preferably 0.005–0.01 w/v % relative to the entire suspension.

The suspension of the present invention may comprise an isotonizing agent to isotonize the suspension with tears. Examples of the isotonizing agent include sodium chloride, glycerol, glucose, mannitol and sorbitol, which are conventionally used for eye drops. Of these, sodium chloride is preferable as it possesses superior dispersibility when formulated into a preparation, suppresses formation of agglomerates and provides a suspension superior in redispersibility. The isotonizing agent is added in such an amount that makes the osmotic pressure of the suspension identical to that of tears.

The suspension of the present invention may include a buffer. The buffer should have buffer capacity in the range of pH 3–8. Examples of the buffer include acetates such as sodium acetate; phosphates such as sodium dihydrogenphosphate, disodium hydrogenphosphate, potassium dihydrogenphosphate and dipotassium hydrogenphosphate; ε-aminocaproic acid; amino acid salts such as sodium glutamate; and boric acid and a salt thereof. Of the mentioned buffers, acetates and ε-aminocaproic acid are preferable as they suppress formation of agglomerates, prevent lowering of pH, and provide a suspension superior in redispersibility and stability. As the acetate, sodium acetate is particularly preferable. The buffer is generally contained in a proportion of 0.01–2.0 w/v %, preferably 0.05–0.5 w/v % relative to the entire suspension.

The suspension of the present invention may comprise a nonionic surfactant for enhancing dispersion stability. The nonionic surfactant to be used in the present invention is non-toxic, non-irritant and applicable to the eye. Examples of the nonionic surfactant to be used in the present invention include polyoxyethylenesorbitan fatty acid esters such as polyoxyethylenesorbitan monooleate, polyoxyethylenesorbitan monolaurate, polyoxyethylenesorbitan monopalmitate and polyoxyethylenesorbitan monostearate; polyoxyethylene hydrogenated castor oils; sorbitan fatty acid esters such as sorbitan monooleate, sorbitan monolaurate, sorbitan monopalmitate and sorbitan monostearate; polyoxyethylene polyoxypropylene polymer; polyoxyethylene alkyl ethers such as polyoxyethylene lauryl ether; and polyoxyethylene fatty acid esters such as polyoxyethylene monostearate.

Of the recited nonionic surfactants, polyoxyethylenesorbitan fatty acid esters and polyoxyethylene hydrogenated castor oils are preferable, since they suppress formation of agglomerates, prevent lowering of pH, and provide a suspension superior in redispersibility and stability. The polyoxyethylenesorbitan fatty acid esters preferably have 16–18 carbon atoms in the fatty acid moiety and preferably have an ethylene oxide average addition molar number of about 20. Particularly preferred is Polysorbate 80 [polyoxyethylene (20) sorbitan monooleate, ethylene oxide average addition molar number; about 20]. The ethylene oxide average addition molar number of polyoxyethylene hydrogenated castor oils is preferably about 40–60. The nonionic surfactant is generally contained in a proportion of 0.005–1.0 w/v %, preferably 0.01–0.5 w/v % and more preferably 0.05–0.2 w/v % relative to the entire suspension.

The ophthalmic suspension of the present invention may contain various additives such as a stabilizer, an antioxidant, a chelating agent, a pH adjusting agent, a thickener and an absorption promoter. Examples of the antioxidant include ascorbic acid, sodium ascorbate, tocopherol, sodium thiosulfate and sodium hydrogensulfite. Examples of the chelating agent include sodium edetate (disodium ethylenediamine tetraacetate) and sodium citrate. Examples of the pH adjusting agent include hydrochloric acid, citric acid, phosphoric acid, acetic acid, tartaric acid, sodium hydroxide, potassidum hydroxide, sodium carbonate and sodium hydrogencarbonate.

The suspension of the present invention is generally adjusted to pH 4–6, the range in which difluprednate is stable and less irritating to the mucosal membrane of the eye. The average particle size of the suspended difluprednate is 0.01–75 µm, preferably 0.1–20 µm. The use of the difluprednate in this particle size range affords a suspension having superior dispersibility, which is less irritating to the mucosal membrane of the eye.

The ophthalmic suspension of the present invention can be prepared according to known production methods of a suspension, by suspending difluprednate in a pharmaceutically acceptable solvent. For example, additives such as a water soluble polymer, a buffer, an isotonizing agent and a preservative are added as necessary to a pharmaceutically acceptable aqueous solvent; the pH is adjusted to 4–6 with a pH adjusting agent such as hydrochloric acid and an aqueous solution of sodium hydroxide; and difluprednate is suspended to give a uniform suspension. For providing a uniform suspension, a known homogenizing means such as a mixer, a homogenizer and an ultrasonic treatment can be used. The ophthalmic suspension is prepared by sterile manipulation or subjected to sterilization at a suitable stage.

Also, the ophthalmic suspension of the present invention can be provided as a disposable ophthalmic preparation without a preservative. The disposable ophthalmic suspension is packaged as a single dose in a sealed container to be opened when in use. When formulated into a disposable preparation, a preservative as mentioned above may not be contained, since contamination with a microorganism does not occur.

The present invention is described in more detail by illustrative Examples and Experimental Examples to be given below.

| | |
|---|---|
| Difluprednate | 0.1 g |
| Sodium acetate | 0.1 g |
| Sodium chloride | 0.8 g |
| Benzalkonium chloride | 0.005 g |
| Hydroxypropylmethylcellulose | 0.2 g |
| Polyoxyethylene hydrogenated castor oil 60 | 0.05 g |
| Hydrochloric acid | suitable amount |
| Distilled water | amount to make the total 100 ml |

The prescribed amount of hydroxypropylmethylcellulose is dissolved in about 80 ml of distilled water heated to about 70° C. and the mixture is cooled to about 40° C. Then, polyoxyethylene hydrogenated castor oil 60 (ethylene oxide average addition molar number; about 60) is dissolved therein. The mixture is cooled to room temperature, and sodium acetate, sodium chloride and benzalkonium chloride are dissolved therein. The pH is adjusted to 5.0 with hydrochloric acid and difluprednate is suspended. Distilled water is added to make the total amount 100 ml.

EXAMPLE 2

| | |
|---|---|
| Difluprednate | 0.05 g |
| Sodium acetate | 0.1 g |
| Sodium chloride | 0.8 g |
| Benzalkonium chloride | 0.005 g |
| Hydroxypropylmethylcellulose | 0.2 g |
| Hydrochloric acid | suitable amount |
| Distilled water | amount to make the total 100 ml |

The prescribed amount of hydroxypropylmethylcellulose is dissolved in about 80 ml of distilled water heated to about 70° C. and the mixture is cooled to room temperature. Then, sodium acetate, sodium chloride and benzalkonium chloride are dissolved therein. The pH is adjusted to 5.0 with hydrochloric acid and difluprednate is suspended. Distilled water is added to make the total amount 100 ml.

EXAMPLE 3

| | |
|---|---|
| Difluprednate | 0.05 g |
| ε-Aminocaproic acid | 0.1 g |
| Sodium chloride | 0.8 g |
| Benzalkonium chloride | 0.005 g |
| Chlorhexidine gluconate | 0.002 g |
| Polyvinyl alcohol | 0.2 g |
| Polysorbate 80 | 0.05 g |
| Hydrochloric acid | suitable amount |
| Distilled water | amount to make the total 100 ml |

The prescribed amount of polyvinyl alcohol is dissolved in about 80 ml of distilled water heated to about 40° C. and the mixture is cooled to room temperature. Then, ε-aminocaproic acid, sodium chloride, benzalkonium chloride, chlorhexidine gluconate and Polysorbate 80 are dissolved therein. The pH is adjusted to 6.0 with hydrochloric acid and difluprednate is suspended. Distilled water is added to make the total amount 100 ml.

EXAMPLE 4

| | |
|---|---|
| Difluprednate | 0.05 g |
| Sodium dihydrogenphosphate | 0.1 g |
| Sodium chloride | 0.8 g |
| Benzethonium chloride | 0.005 g |
| Polyvinyl alcohol | 0.2 g |
| Sodium hydroxide | suitable amount |
| Distilled water | amount to make the total 100 ml |

The prescribed amount of polyvinyl alcohol is dissolved in about 80 ml of distilled water heated to about 40° C. and the mixture is cooled to room temperature. Then, sodium dihydrogenphosphate, sodium chloride and benzethonium chloride are dissolved therein. The pH is adjusted to 6.0 with sodium hydroxide and difluprednate is suspended. Distilled water is added to make the total amount 100 ml.

Experimental Example 1 (Stability test)

The ophthalmic suspensions having the compositions shown in Table 1 were prepared. The suspensions were packed in 5 ml glass ampoules and stored at 60° C. Visual observation of appearance, property determination after redispersion by shaking and measurement of pH were performed. The property after redispersion by shaking was determined by evaluating the suspension containing particles having a particle size of not more than 75 μm as "fine particles"; the suspension containing agglomerated particles having greater particle sizes and incapable of being redispersed into fine particles as "agglomerates"; and the suspension containing agglomerated particles forming a hard deposit layer on the bottom surface of a container and incapable of redispersion as "caking".

TABLE 1

| Composition | | | A | B | C | D | E | F | G | H |
|---|---|---|---|---|---|---|---|---|---|---|
| Difluprednate | | | 0.05 | 0.05 | 0.05 | 0.05 | 0.05 | 0.05 | 0.05 | 0.05 |
| Suspending agent | Water soluble polymer | HPMC | 0.2 | 0.2 | | 0.2 | 0.2 | 0.2 | 0.2 | 0.2 |
| | | PVA (EG40) | | | 0.2 | | | | | |
| | Surfactant | Polysorbate 80 | | | | | | | 0.1 | |
| | | HCO60 | | | | | | | | 0.05 |
| Buffer | Sodium acetate | | 0.1 | | | 0.1 | 0.1 | 0.1 | 0.1 | 0.1 |
| | ε-aminocaproic acid | | | 0.1 | | | | | | |
| Preservative | Benzalkonium chloride | | | | | 0.005 | 0.005 | 0.005 | 0.005 | 0.005 |
| | Chlorhexidine gluconate | | | | | | | 0.002 | | |
| Isotonizing agent | Sodium chloride | | | | | | 0.8 | 0.8 | 0.8 | 0.8 |

Note:
HPMC hydroxyproplmethylcellulose (unit; w/v%)
PVA(EG40) polyvinyl alcohol
HCO60 polyoxyethylene hydrogenated castor oil 60

The results are shown in Table 2. While deposits of suspended particles were observed in every composition, they redispersed into fine particles by shaking. When hydroxypropylmethylcellulose (HPMC) was used as a suspending agent and sodium acetate or ε-aminocaproic acid was used as a buffer, neither agglomerates nor caking was formed. Moreover, pH showed no change, and stable suspensions were obtained (compositions A and B). When polyvinyl alcohol (PVA) was used as a suspending agent, a stable suspension was obtained (composition C). The use of benzalkonium chloride and/or chlorhexidine gluconate as a preservative resulted in the absence of agglomerates and caking, and stable suspensions were obtained with minor changes in pH (compositions D, E and F). The use of sodium chloride as an isotonizing agent resulted in suspensions having superior redispersibility and stability (compositions E and F). Furthermore, stable suspensions were obtained when a nonionic surfactant such as Polysorbate 80 and polyoxyethylene hydrogenated castor oil 60 (HC060), was used as a suspending agent (compositions G and H).

The above results demonstrate that the combination of HPMC as a suspending agent and sodium acetate or ε-aminocaproic acid as a buffer makes the suspension stable and such stability can be maintained even if benzalkonium chloride and chlorhexidine gluconate are added as preservatives and sodium chloride is added as an isotonizing agent. The addition of a surfactant did not affect said stability.

1, wherein each value is the mean±standard error (n=6–7) and the mark "*" indicates presence of a significant difference from the control, p<0.01. In contrast to the increase in the protein concentration of the aqueous humor in the control group to 23.8 mg/ml, the group administered with a difluprednate suspension showed strong inflammation suppressing effect as evidenced by the protein concentrations of 3.6 mg/ml at a 0.02% difluprednate concentration and 1.4 mg/ml at a 0.1% difluprednate concentration. The suppression ratio was 84.7% and 94.0%, respectively. The protein concentration of the aqueous humor in the group administered with 0.1% betamethasone was 9.1 mg/ml and the suppression ratio was 61.9%.

TABLE 2

| | Property after redispersion | | | | pH | | | |
|---|---|---|---|---|---|---|---|---|
| | on preparation | 1 week later | 2 weeks later | 4 weeks later | on preparation | 1 week later | 2 weeks later | 4 weeks later |
| A | fine particle | fine particle | fine particle | fine particle | 5.00 | | | 5.00 |
| B | fine particle | fine particle | fine particle | fine particle | 5.00 | | | 5.00 |
| C | fine particle | fine particle | fine particle | fine particle | 4.97 | 5.04 | 5.07 | 5.01 |
| D | fine particle | | | fine particle | 4.98 | | | 4.88 |
| E | fine particle | fine particle | fine particle | fine particle | 4.62 | 4.59 | 4.62 | 4.63 |
| F | fine particle | fine particle | fine particle | fine particle | 4.93 | 5.00 | 5.01 | 5.04 |
| G | fine particle | fine particle | fine particle | fine particle | 5.08 | 4.87 | 4.70 | 4.69 |
| H | fine particle | fine particle | fine particle | fine particle | 4.91 | 4.89 | 4.75 | 4.70 |

Experimental Example 2 (Antiinflammatory action on acute uveitis)
(1) Test animals
  Male Japanese albino rabbits weighing about 2.2 kg.
(2) Test drug
  Difluprednate was suspended to a concentration of 0.02% or 0.1% in a base solution having the following composition. The pH was adjusted to 7.0. As a control drug, 0.1% betamethasone [Rinderon (trademark) solution, manufactured by Shionogi & Co., Ltd.] was used. A physiological saline was administered to the control group.

| Composition | |
|---|---|
| Sodium dihydrogen-phosphate dihydrate | 0.1 w/v% |
| Polysorbate 80 | 0.1 w/v% |
| Sodium chloride | 0.852 w/v% |
| Sodium hydroxide | suitable amount |
| Distilled water | amount to make the total 100 w/v% |

(3) Test method
  E. coli endotoxin dissolved in physiological saline was intravenously administered to the rabbits by 10 μg/ml/kg to induce ocular inflammation. The test drug (50 μl) was instilled in one eye of the rabbits 1 hour before the injection of the endotoxin. Four hours after inducing inflammation, aqueous humor of the instilled eye was taken and protein concentration of the aqueous humor was measured by the Lowry method [J. Bio. Chem., 193–265 (1951)].
(4) Results
  The protein concentration of the aqueous humor 4 hours after the intravenous injection of endotoxin is shown in FIG.

Based on the aforementioned results, it is evident that the ophthalmic suspension of the present invention has stronger antiinflammatory action than a betamethasone eye drop and is an effective drug against uveitis.

Experimental Example 3 (Suppression of I-type allergic reaction in rat)
(1) Test animals
  Forty male Wistar rats weighing about 100 g, purchased from Japan Clare Corp.
(2) Test drug
  In the same manner as in Experimental Example 2, 0.01%, 0.03% and 0.1% difluprednate suspensions were prepared. As a control drug, 0.1% betamethasone [Rinderon (trademark) solution, manufactured by Shionogi & Co., Ltd.] was used. A physiological saline was administered to the control group.
(3) Test method
  Anti-rat egg albumin serum was diluted 64 fold with physiological saline and 50 μl thereof was injected to the rats under the conjunctiva of the upper eyelid of one eye of the rats to allow passive sensitization. Seventy-two hours after the injection under the conjunctiva, 1 ml of a mixture of an equivalent 1% egg albumin and an equivalent 1% Evans blue was injected from the tail vein to induce passive anaphylactic reaction at the local site of conjunctiva. Thirty minutes later, the eyelid was removed and the dye was extracted overnight with 3 ml of formamide. The absorption at 625 nm was measured. The test drug (5 μl) was instilled in the sensitized eye three and four hours prior to the passive anaphylactic reaction.
(4) Results The amount of the dye leaked and suppression of rat passive anaphylactic reaction is shown in Table 3.

TABLE 3

| Test drug | Concentration (%) | n | Amount of dye leaked (μg/site) | Suppression (%) |
|---|---|---|---|---|
| Physiological saline | — | 8 | 24.57 ± 7.00 | — |
| Difluprednate | 0.01 | 8 | 11.01 ± 2.61 | 55.2 |
|  | 0.03 | 8 | 7.42 ± 0.53* | 69.8 |
|  | 0.1 | 8 | 5.75 ± 0.50* | 76.6 |
| Betamethasone | 0.1 | 8 | 21.08± 6.11 | 14.2 |

Each value is the mean±standard error. The mark "*" indicates presence of a significant difference from the control, $p<0.05$ (Dunnett's test)

As the results show, the amount of dye leaked in the control group was 24.57 μg/site, whereas the group administered with an eye drop of a difluprednate suspension showed 55.2% suppression at 0.01% concentration, 69.8% suppression at 0.03% concentration and 76.6% suppression at 0.1% concentration, demonstrating significant suppressive action. In contrast, the group administered with 0.1% betamethasone showed 14.2% suppression and the suppressive effect was not significant.

Based on the aforementioned results, it is evident that the ophthalmic suspension of the present invention is an effective drug against I-type allergic reaction.

Experimental Example 4 (Antiinflammatory action against external ophthalmic inflammation)

(1) Test animals

Male Wistar rats weighing about 120 g, purchased from Japan Clare Corp.

(2) Test drug

Difluprednate was suspended at a concentration of 0.01%, 0.03% or 0.1% in a base solution having the following composition. The pH was adjusted to 5.0. As a control drug, 0.1% betamethasone [Rinderon (trademark) solution, manufactured by Shionogi & Co., Ltd.] was used. A physiological saline was administered to the control group.

| Composition | |
|---|---|
| Sodium dihydrogenphosphate dihydrate | 0.1 w/v % |
| Hydroxypropylmethylcellulose | 0.2 w/v % |
| Sodium chloride | 0.9 w/v % |
| Distilled water | amount to make the total 100 w/v % |

(3) Test method

In one eye of the rats was instilled 30% croton oil (5 μl) dissolved in carbitol three times at 60 min intervals to induce edema in the palpebral conjunctiva. Two hours after the final instillation, the edematized region of the palpebral conjunctiva was removed and weighed. Each test drug (5 μl) was instilled to the eye to be challenged, 30 minutes prior to the initial croton oil instillation.

(4) Results

Figure 2:
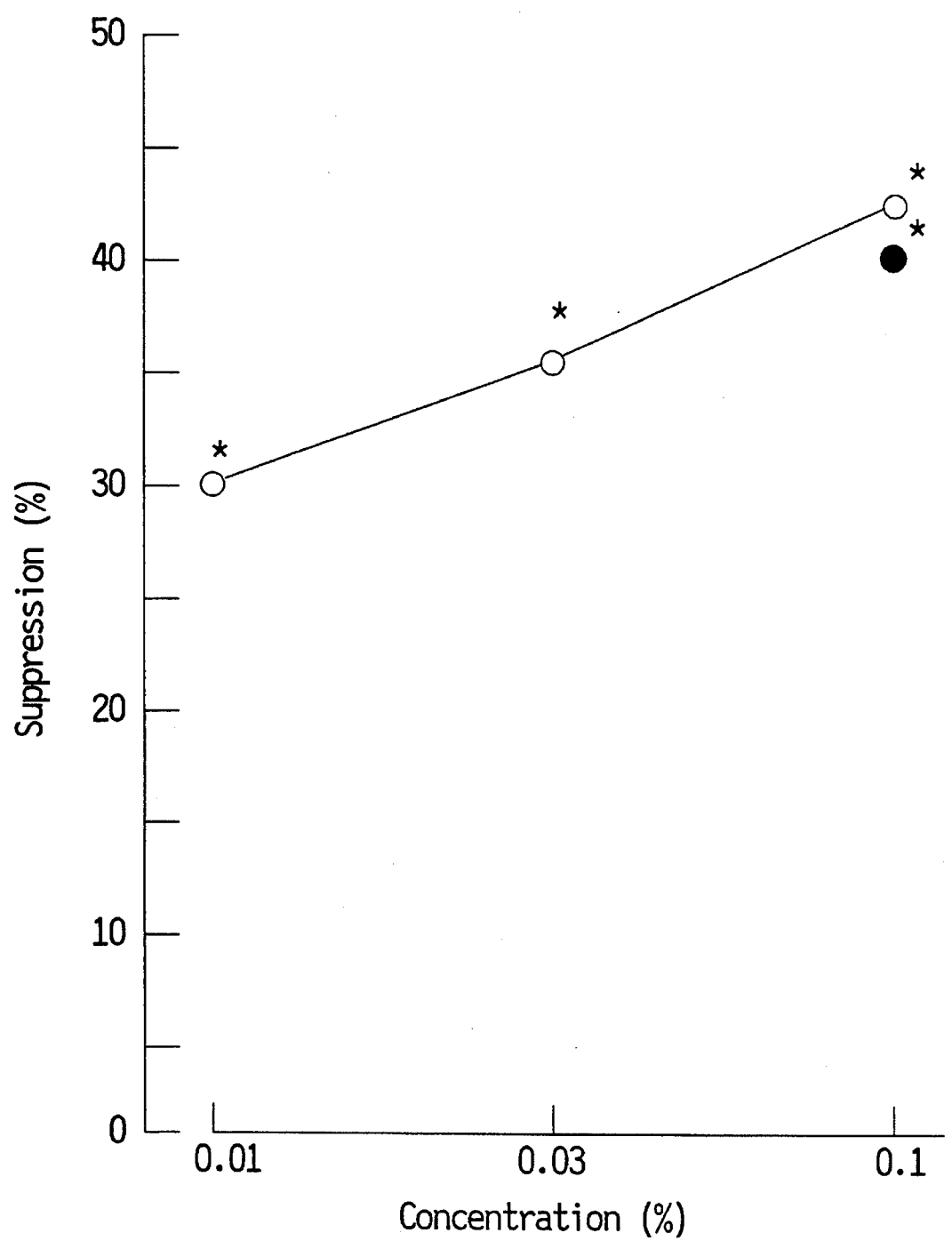
FIG. 2 is a graph showing the results of Experimental Example 4, wherein each value is average (n=10) and the mark "*" indicates presence of a significant difference from the control, $p<0.01$.

The results are shown in Table 4 and FIG. 2, wherein each value is average (n=10) and the mark "*" indicates presence of a significant difference from the control, $p<0.01$.

TABLE 4

| Test drug | Concentration (%) | Dose (μg) | n | Edema weight (mg) | Suppression (%) |
|---|---|---|---|---|---|
| Physiological saline | — | | 10 | 21.1 ± 1.4 | — |
| Difluprednate | 0.01 | 1 | 10 | 15.0 ± 0.8* | 28.9 |
|  | 0.03 | 3 | 10 | 13.7 ± 0.9* | 35.1 |
|  | 0.1 | 10 | 10 | 12.2 ± 0.7* | 42.2 |
| Betamethasone | 0.1 | 10 | 10 | 13.3 ± 0.9* | 37.0 |

Each value is the mean±standard error. The mark "*" indicates presence of a significant difference from the control, $p<0.01$ (Dunnett's test)

As the results show, the edema weight in the control group was 21.1 mg, whereas the group administered with an eye drop of a difluprednate suspension showed significant dose-dependent suppressive effects. The suppression at 0.01%, 0.03% and 0.1% concentration was 28.9%, 35.1% and 42.2% respectively. The group administered with 0.1% betamethasone showed 37.0% suppression.

Based on these results, it is evident that the ophthalmic suspension of the present invention shows concentration-dependent suppressive effects against rat conjunctival edema induced by croton oil, and is an effective drug for external ophthalmic inflammation.

The ophthalmic suspension of the present invention shows superior antiinflammatory action and antiallergic action by local administration. Accordingly, the suspension of the present invention is useful for the treatment and prevention of disorders of the eye, such as allergic conjunctivitis, vernal conjunctivitis, blepharitis marginalis, catarrhal conjunctivitis and uveitis.

The suspension of the present invention can be administered by instillation to the eye and is more advantageous than conventional eye ointments containing difluprednate, in that local administration to the eye is readily performed. In addition, the suspension for instillation of the present invention can provide, by the administration of a less dose of difluprednate, the pharmacological effects equal to or greater than the effects obtained with conventional betamethasone eye drops. Therefore, the dose and the administration frequency can be reduced.

According to the present invention, moreover, addition of suitable ingredients results in the provision of an ophthalmic suspension of difluprednate, which has good dispersibility when formulated into a preparation and superior redispersibility and stability, that is ascribed to the suppression of secondary particles and caking caused by agglomeration, and suppression of lowered pH.

What is claimed is:

1. An ophthalmic suspension comprising difluprednate as an active ingredient, at least one water soluble polymer selected from the group consisting of hydroxypropylmethylcellulose and polyvinyl alcohol, and at least one buffer selected from the group consisting of sodium acetate and ε-aminocaproic acid.

2. The suspension of claim 1, wherein the water soluble polymer is present in a proportion of 0.05–0.2 w/v %.

3. The suspension of claim 1, further comprising a preservative.

4. The suspension of claim 3, wherein the preservative is at least one member selected from the group consisting of quaternary ammonium salts and cationic compounds.

5. The suspension of claim 4, wherein the quaternary ammonium salt is at least one member selected from the group consisting of benzalkonium chloride and benzethonium chloride.

6. The suspension of claim 4, wherein the cationic compound is chlorhexidine gluconate.

7. The suspension of claim 3, wherein the preservative is comprised in a proportion of 0.005–0.01 w/v %.

8. The suspension of claim 4, wherein the preservative is comprised in a proportion of 0.005–0.01 w/v %.

9. The suspension of claim 1, further comprising an isotonizing agent.

10. The suspension of claim 9, wherein the isotonizing agent is sodium chloride.

11. The suspension of claim 1, further comprising a preservative and an isotonizing agent.

12. The suspension of claim 11, wherein the preservative is at least one member selected from the group consisting of benzalkonium chloride, benzethonium chloride and chlorhexidine gluconate; and the isotonizing agent is sodium chloride.

* * * * *